(12) United States Patent
Drevik

(10) Patent No.: US 8,882,734 B2
(45) Date of Patent: Nov. 11, 2014

(54) LUBRICATED TAMPON HAVING INVERTIBLE FLAPS FOR FACILITATED INSERTION AND REMOVAL

(75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 522 days.

(21) Appl. No.: 13/262,859

(22) PCT Filed: Apr. 6, 2009

(86) PCT No.: PCT/SE2009/050356
§ 371 (c)(1),
(2), (4) Date: Nov. 3, 2011

(87) PCT Pub. No.: WO2010/117309
PCT Pub. Date: Oct. 14, 2010

(65) Prior Publication Data
US 2012/0053544 A1    Mar. 1, 2012

(51) Int. Cl.
*A61F 13/20*    (2006.01)
(52) U.S. Cl.
USPC .................. 604/385.18; 604/385.17; 604/904
(58) Field of Classification Search
USPC ................................ 604/385.17, 385.18, 904
See application file for complete search history.

(56) References Cited

U.S. PATENT DOCUMENTS

| 2,219,886 | A1 | 7/2004 | Lochte et al. |
|---|---|---|---|
| 2005/0080393 | A1 | 4/2005 | Policappelli |
| 2005/0143708 | A1 | 6/2005 | Hagberg et al. |
| 2006/0258971 | A1 | 11/2006 | Chase et al. |
| 2007/0135787 | A1 | 6/2007 | Raidel et al. |

FOREIGN PATENT DOCUMENTS

| EP | 1345560 | 9/2003 |
|---|---|---|
| GB | 2 056 283 | 3/1981 |
| RU | 2219886 | 12/2003 |
| WO | WO 02/49556 | 6/2002 |
| WO | 2005/051270 | 6/2005 |
| WO | WO 2005/063131 | 7/2005 |
| WO | 2008/002216 | 1/2008 |

OTHER PUBLICATIONS

Decision on Grant in corresponding Russian Patent Application No. 2011144824 (with English translation thereoef) (8 pages), Dec. 10, 2012.

*Primary Examiner* — Jacqueline F. Stephens
(74) *Attorney, Agent, or Firm* — Drinker Biddle & Reath LLP

(57) ABSTRACT

A tampon including an absorption body enclosed in a cover. The tampon has an insertion end and a withdrawal end and further includes at least one withdrawal string. The cover includes a plurality of first invertible flaps or a plurality of second invertible flaps, or a combination thereof. Each first invertible flap is constituted by a portion of the cover and is arranged to be moved between a first initial position and a first inverted position during withdrawal of the tampon out of the vagina of a user so as to aid the withdrawal. Each second invertible flap is constituted by a portion of the cover and is arranged to be moved between a second initial position and a second inverted position during insertion of the tampon into the vagina of a user so as to aid the insertion.

23 Claims, 7 Drawing Sheets

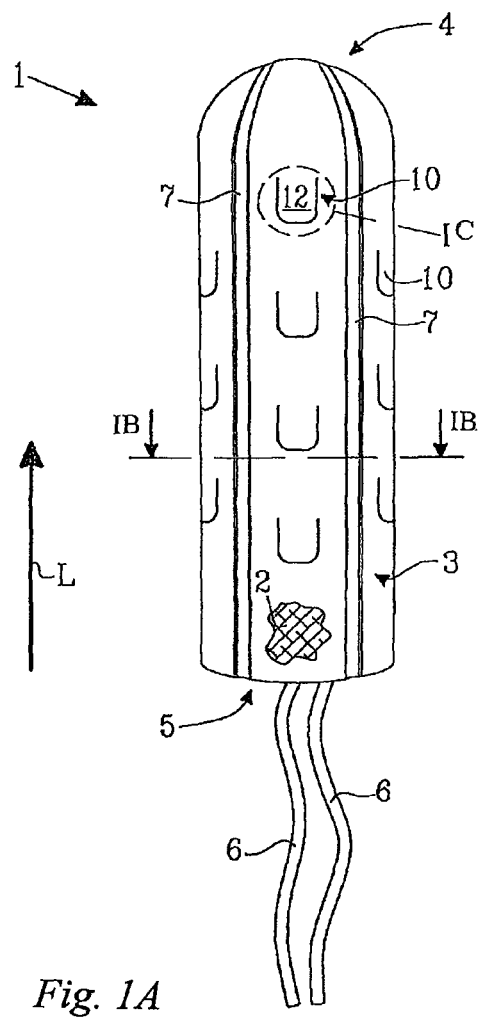
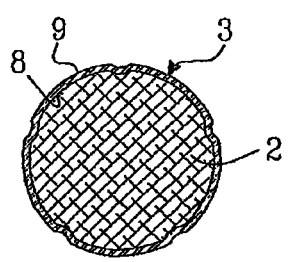
Fig. 1B
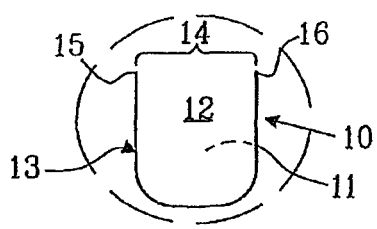
Fig. 1C
Fig. 1A

LUBRICATED TAMPON HAVING INVERTIBLE FLAPS FOR FACILITATED INSERTION AND REMOVAL

CROSS-REFERENCE TO PRIOR APPLICATION

This application is a §371 National Stage Application of PCT International Application No. PCT/SE2009/050356 filed Apr. 6, 2009, which is incorporated herein in its entirety.

TECHNICAL FIELD

The present disclosure relates to a tampon including an elongated absorption body at least partly enclosed in a liquid permeable cover. The tampon has an insertion end and a withdrawal end and further includes at least one withdrawal string extending from the withdrawal end.

BACKGROUND

Menstrual tampons for intra-vaginal use have been known and used for a very long time. Since tampons are worn internally, they are considered to be discrete and mostly very comfortable to wear, lacking the occluding plastic backing of external protection devices such as sanitary napkins. However, during days of light menstrual flow or when changing the tampon after a short period of use, removal of the tampon may cause severe discomfort or even pain. This is due to the tampon absorbing menstrual discharge as well as humidity from the mucous membranes on the vaginal wall. When the tampon is being removed, it tends to adhere to the vaginal wall giving rise to increased friction and making it hard to extract. Moreover, the dried-out mucous membranes make it almost impossible or at least very difficult and uncomfortable to insert a new tampon to replace the one that has been removed.

The problems experienced when changing tampons that have not been used to their full capacity lead to users wearing tampons for longer periods of time than recommended. This is highly undesirable in that it increases the risk of bacterial infections.

In order to facilitate removal of a used tampon, it has been suggested to treat the surface of the tampon with lubricating agents decreasing the friction between the tampon and the vaginal wall. However, such treatment suffers from several drawbacks. For example, lubricating agents provided on the surface of the tampon may easily migrate onto and/or into a packaging enclosing the tampon before use. Furthermore, the use of lubricating agents on the surface of the tampon complicates the production process and puts particular demands on handling and packaging of the tampons.

Furthermore, in order to facilitate removal of a used tampon, it has also been suggested to provide the tampon with a withdrawal aid. For example, US 2005/0143708 discloses a tampon including a withdrawal aid, which is attached to and extends from the insertion end of the tampon. The withdrawal aid is positioned in a first position before use of the tampon and in the insertion state of the tampon. In the first position, the withdrawal aid covers at least parts of the length of the absorption body and acts as a spacing means, creating a distance between the mucous membranes on the user's vaginal wall and the absorption body. However, when the tampon is being pulled out after use, the withdrawal aid will move from the first position to a second position in which it extends away from the absorption body. The withdrawal aid will move from the first position to the second position by inverting or peeling away from the absorption body. Thereby, removal of the tampon is facilitated and chafing and abrasion of the mucous membranes are reduced.

However, the process for producing the tampon with the withdrawal aid disclosed in US 2005/0143708 is relatively complicated. In addition, during withdrawal of the tampon disclosed in US 2005/0143708 out of the vagina, the user might experience that the tampon is relatively long due to the inverted withdrawal aid extending away from the absorption body.

Thus, there still exists a need for an improved vaginal tampon, whose removal from the vagina is facilitated even when only partially saturated with menstrual fluid and/or whose insertion into the vagina is facilitated, and which is not associated with the above mentioned drawbacks.

SUMMARY

Accordingly, it is desired to provide an improved tampon. The tampon includes an elongated absorption body at least partly enclosed in a liquid permeable cover. The tampon has an insertion end and a withdrawal end and further includes at least one withdrawal string extending from said withdrawal end.

In a first embodiment, the liquid permeable cover includes a plurality of first invertible flaps and/or a plurality of second invertible flaps.

The first invertible flap is constituted by a portion of said cover and includes a first inner surface and an opposite first outer surface. The first invertible flap is partly detached from the remainder of said cover by means of a first slit system provided in said cover and is connected with the remainder of said cover via a first fold line. The first invertible flap is delimited by said first fold line and said first slit system. The first fold line extends along a line between a first start point and a first end point. The first slit system includes at least one slit and extends along a first curve starting from said first start point and ending in said first end point, said first curve bulging away from said first fold line towards said withdrawal end. The first slit system and said first fold line are provided such that said first invertible flap is arranged to be moved between a first initial position and a first inverted position during withdrawal of said tampon out of the vagina of a user so as to aid said withdrawal. The first invertible flap is arranged to be moved between said first initial position and said first inverted position by being folded around said first fold line. The first invertible flap is positioned in said first initial position before use of said tampon, and said first inner surface faces said absorption body in said first initial position and faces away from said absorption body in said first inverted position.

The second invertible flap is constituted by a portion of said cover and includes a second inner surface and an opposite second outer surface. The second invertible flap is partly detached from the remainder of said cover by means of a second slit system provided in said cover and is connected with the remainder of said cover via a second fold line. The second invertible flap is delimited by said second fold line and said second slit system, said second fold line extending along a line between a second start point and a second end point. The second slit system includes at least one slit and extends along a second curve starting from said second start point and ending in said second end point, said second curve bulging away from said second fold line towards said insertion end. The second slit system and said second fold line are provided such that said second invertible flap is arranged to be moved between a second initial position and a second inverted position during insertion of said tampon into the vagina of a user so as to aid said insertion. The second invertible flap is arranged to be moved between said second initial position and said second inverted position by being folded around said second fold line. The second invertible flap is positioned in said second initial position before use of said tampon, and said second inner surface faces said absorption body in said second initial position and faces away from said absorption body in said second inverted position.

Preferred embodiments are listed in the dependent claims.

Still other objects and features will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views:

FIG. 1A is a side view of a first embodiment of a tampon when the first invertible flaps are positioned in a first initial position;

FIG. 1B is a cross-sectional view according to line IB-IB in FIG. 1A;

FIG. 1C is an enlarged view of a first invertible flap of the tampon in FIG. 1A;

DETAILED DESCRIPTION OF PREFERRED EMBODIMENTS

Figure 1D:
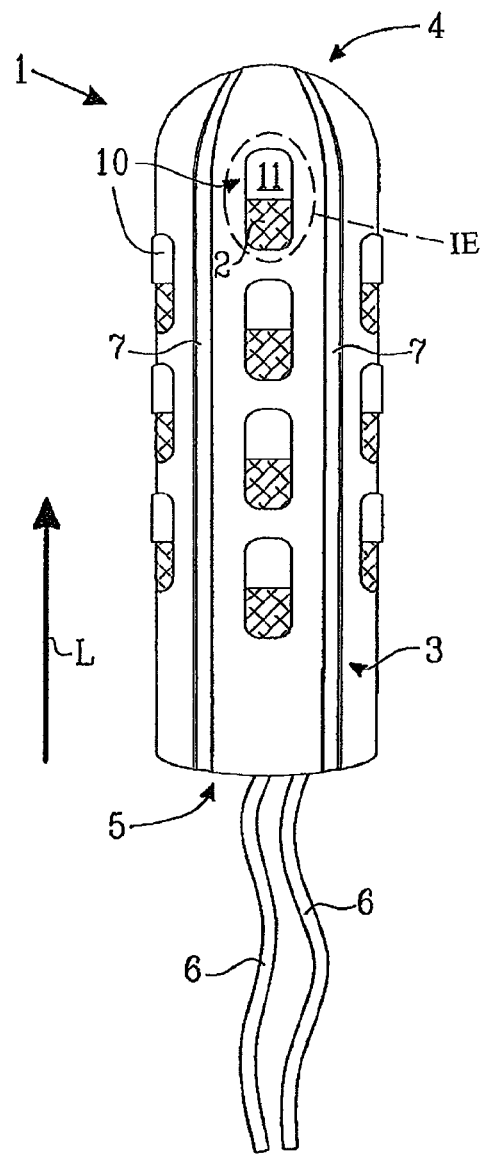
FIG. 1D is a side view of the first embodiment of the tampon when the first invertible flaps are positioned in a first inverted position.

As mentioned previously, the disclosure concerns a vaginal tampon. Embodiments of the invention will be described in more detail in the following with reference to the accompanying drawings.

FIG. 1A shows a side view of a first embodiment of a tampon 1 and FIG. 1B shows a cross-sectional view of the first embodiment of the tampon 1 according to line IB-IB in FIG. 1A. The tampon 1 includes an elongated absorption body 2 enclosed in a liquid permeable cover 3. The cover 3 minimizes linting from the absorption body 2. In the first embodiment shown in FIG. 1A, the absorption body 2 has a generally cylindrical shape. However, the absorption body 2 may alternatively have any other suitable shape, such as e.g. conical, pointed, cup-shaped, banana-shaped or the like. Furthermore, the tampon 1 has an insertion end 4 and a withdrawal end 5. The insertion end 4 may have any suitable shape, such as e.g. rounded (FIG. 1A), blunt (not shown) or pointed (not shown). Equally, the withdrawal end 5 may have any suitable shape, such as e.g. blunt (FIG. 1A), rounded (not shown) or pointed (not shown).

The term "insertion end" is herein defined as that part of the tampon, including the tip of the tampon that is arranged to be firstly introduced into the vagina of a user. The term "withdrawal end" is herein defined as that part of the tampon that is arranged to constitute the leading end (except for the withdrawal strings) of the tampon during withdrawal of the tampon out of the vagina of a user.

In the first embodiment, the absorption body 2 is completely enclosed in the cover 3 (FIG. 1A). However, the absorption body 2 may alternatively be only partly enclosed in the cover 3. For example, the cover 3 may be arranged to cover only the length of the absorption body 2 leaving one or both of the insertion end 4 and the withdrawal end 5 free from cover material. Alternatively, the absorption body 2 may be covered by the cover 3 only at, or in parts near, the insertion end 4 and/or the withdrawal end 5. Thus, the absorption body 2 is at least partly enclosed in the cover 3.

In the first embodiment shown in FIG. 1A, the tampon 1 includes also two withdrawal strings 6 extending from the withdrawal end 5. However, the tampon 1 may alternatively include any other suitable number of withdrawal strings 6 than two withdrawal strings, e.g. one withdrawal string or three withdrawal strings. Thus, the tampon 1 includes at least one withdrawal string 6. In addition, in the first embodiment, the tampon 1 is provided with longitudinally extending compressed grooves 7 that aid liquid distribution along the length of the tampon 1. The provision of such compressed grooves is common in the art, but they may optionally be omitted.

In the first embodiment, the absorption body 2 is a mass of absorbent fibres that has been compressed into a roughly cylindrical shape (FIG. 1B). However, the absorption body 2 may be constructed by any conventional method. For example, the absorption body 2 may alternatively be constructed by rolling a layer of absorbent material to a roughly cylindrical shape and thereafter compressing the cylindrical shape (not shown). Examples of methods of constructing the tampon will be further described below. Suitable absorbent materials for the absorption body 2 are cellulose fibres such as rayon, cotton and cellulose fluff pulp. The absorption body 2 may also include a binder such as thermoplastic fibres. Polymeric gelling materials, also known as superabsorbents, can be used as well as bacteria inhibiting agents.

The cover 3 includes an inner surface 8 facing the absorption body 2 and an outer surface 9 facing away from the absorption body 2 (FIG. 1B). The cover 3 may be any suitable non-abrasive liquid permeable material. In particular embodiments, the cover 3 is a nonwoven material which may be a spunbonded, carded or spunlaced web made of polypropylene, polyethylene, viscose, bicomponent fibers or any other suitable fibrous material. However, perforated plastic films, cast or knitted nettings or similar porous materials may also be used. The cover 3 may be constituted by one or more material layers. Thus, the cover 3 may be a laminate. In addition, the cover 3 may have different friction characteristics on the inner surface 8 and the outer surface 9. For example, the inner surface 8 may be smoother than the outer surface 9.

The withdrawal strings 6 are made from a material having high tensile strength and are firmly attached to the remainder of the tampon 1 by being wound internally in the absorption body 2 or by being welded, glued or sewn to the absorption body 2 and/or to the liquid permeable cover 3.

In the first embodiment shown in FIG. 1A, the liquid permeable cover 3 includes a plurality of first invertible flaps 10. All first invertible flaps 10 are similar in the first embodiment and FIG. 1C shows an enlarged view of one of the first invertible flaps 10. In the following, one first invertible flap 10 of the plurality of first invertible flaps 10 of the first embodiment will be described with reference to FIGS. 1A and 1C.

The first invertible flap 10 is constituted by a portion of the cover 3 (i.e. the first invertible flap 10 is formed by a part of the cover 3) and includes a first inner surface 11 and an opposite first outer surface 12. The first inner surface 11 of the first invertible flap 10 constitutes a part of the inner surface 8 of the cover 3, and the first outer surface 12 of the first invertible flap 10 constitutes a part of the outer surface 9 of the cover 3.

The first invertible flap 10 is partly detached from the remainder of the cover 3, i.e. one or more border parts of the first invertible flap 10 are detached from (non-connected with) the remainder of the cover 3. The detachment is obtained by means of a first slit system 13 provided in the cover 3. However, the first invertible flap 10 is connected with the remainder of the cover 3 via a first fold line 14. Thus, the first invertible flap 10 is delimited by the first fold line 14 and the first slit system 13, i.e. the first invertible flap 10 is completely surrounded by the first fold line 14 and the first slit system 13.

More specifically, the first fold line 14 extends along a line between a first start point 15 and a first end point 16. Furthermore, the first slit system 13 extends along a first curve starting from the first start point 15 and ending in the first end point 16. In the first embodiment shown in FIGS. 1A and 1C, the first slit system 13 is constituted by one slit extending from the first start point 15 to the first end point 16 along the first curve. The first curve bulges away from the first fold line 14 towards the withdrawal end 5. In the first embodiment, the first curve is U-shaped. Thereby, the slit constituting the first slit system 13 is also U-shaped. The first curve may alternatively have any other suitable shape. This will be further described below.

The term "slit" is herein intended to denote an essentially one-dimensional through going opening in a layer of material, whereby the opening extends from a start point to an end point along a curve and has a depth which depends on the thickness of the cover material and the manner in which the slit is executed in the material. The slit includes two interfaces. When no external forces are present, the two interfaces may be in contact with one another and close the opening in the same way as if the slit were not present, but with the difference that the bonds which otherwise hold the layer of material together are absent in the section of the layer of material in which the slit is present. However, depending on the method and tools for providing the slit, the produced flap or parts of the produced flap (e.g. the free edges thereof) may be moved slightly outwards from the remainder of the cover and/or the free edge(s) of the produced flap may be bent away from the remainder of the cover such that the two interfaces are not, or only partly, in contact with each other. The slit is manufactured by rupturing the bonds in the layer of material over the distance required for the extent of the slit. The bonds may be ruptured, for example, by producing an incision in the layer of material by means of slitting, cutting or in some other way. This is entirely true in a theoretical model, although in practical reality material will disappear on a micrometric scale as a consequence of, for example, blunt tools, etc. The loss of material must not be confused with the loss of material when making holes, where the opening is not one-dimensional, but rather two-dimensional, due to the requirement in the case of holes for material to be removed in such a way that a permanent opening is formed, where corresponding interfaces are not able to make contact with one another if the layer of material is not influenced by external forces. The slit may be made in the cover by means of a through going incision in the cover perpendicular to surfaces of the cover in a plane state, but it may also be made in the cover by means of a through going incision at an angle to the surfaces of the cover in a plane state.

The term "curve" is herein intended to include both curves including two or more linear sections extending in different directions, such as e.g. V-shaped curves or W-shaped curves, and non-linear curves, such as e.g. U-shaped curves. In addition, the curve may be wavy.

The first slit system 13 and the first fold line 14 delimiting the first invertible flap 10 are provided such that the first invertible flap 10 is arranged to be moved between a first initial position (FIGS. 1A and 1C) and a first inverted position (FIGS. 1D and 1E) during withdrawal of the tampon 1 out of the vagina of a user so as to aid the withdrawal. More specifically, the first slit system 13 and the first fold line 14 delimiting the first invertible flap 10 have such an extension and orientation that the first invertible flap 10 is arranged to be moved between a first initial position and a first inverted position during withdrawal of the tampon 1 out of the vagina of a user. Thus, the first invertible flap 10 is shaped and oriented by means of the first slit system 13 and the first fold line 14 such that the first invertible flap 10 is arranged to be moved between a first initial position and a first inverted position during withdrawal of the tampon 1 out of the vagina of a user. The first invertible flap 10 is arranged to be moved between the first initial position and the first inverted position by being folded around the first fold line 14.

The first invertible flap 10 is positioned in the first initial position before use of the tampon 1 (FIGS. 1A and 1C). In the first initial position, the first inner surface 11 of the first invertible flap 10 faces the absorption body 2 and the first outer surface 12 of the first invertible flap 10 faces away from the absorption body 2. However, the first invertible flap 10 is arranged to be moved to the first inverted position (FIGS. 1D and 1E) during withdrawal of the tampon 1 out of the vagina of a user. In the first inverted position, the first inner surface 11 of the first invertible flap 10 faces away from the absorption body 2 and the first outer surface 12 faces the absorption body 2. Thus, in the first inverted position, the first outer surface 12 of the first invertible flap 10 is at least partly in contact with the outer surface 9 of the cover 3, and an opening corresponding to the shape of the first invertible flap 10 is formed in the cover 3, whereby the absorption body 2 is exposed by means of the opening.

In accordance with the above, the slit of the first slit system 13 of the first embodiment includes two interfaces. The two interfaces may be in contact with each other in the first initial position. However, the two interfaces may alternatively not be in contact, or only be partly in contact, with each other in the first initial position due to the fact that the produced first invertible flap 10 or parts thereof is/are moved slightly outwards from the remainder of the cover 3 and/or due to the fact that the free edges of the produced first invertible flap 10 are bent away from the remainder of the cover 3 by means of the utilized method and/or tool for providing the first slit system 13. The expression that "the first inner surface faces the absorption body in the first initial position" is herein intended to include that the complete first inner surface faces the absorption body, or that the main part of the first inner surface faces the absorption body but that one or more free edge portions of the first invertible flap is/are bent away from the remainder of the cover due to influences by the production method and/or tool. Furthermore, in case the first invertible flap or parts thereof is/are moved slightly outwards from the remainder of the cover due to the production method and/or tool, the first inner surface is regarded as facing the absorption body.

As mentioned above, the first slit system 13 and the first fold line 14 delimiting the first invertible flap 10 have such an extension and orientation that the first invertible flap 10 is arranged to be moved between a first initial position and a first inverted position during withdrawal of the tampon 1 out of the vagina of a user. In particular embodiments, as shown in FIGS. 1A and 1C-E, the first fold line 14 extends in a direction orthogonal, or at least essentially orthogonal, to the longitudinal direction L of the tampon 1 in order to contribute to the assurance that the first invertible flap 10 is moved from the first initial position to the first inverted position during withdrawal of the tampon 1. However, the direction in which the first fold line 14 extends may be varied, but it may only be varied to extend in such a direction that it contributes to the assurance that the first invertible flap 10 is moved from the first initial position to the first inverted position during withdrawal of the tampon 1.

Figure 1E:
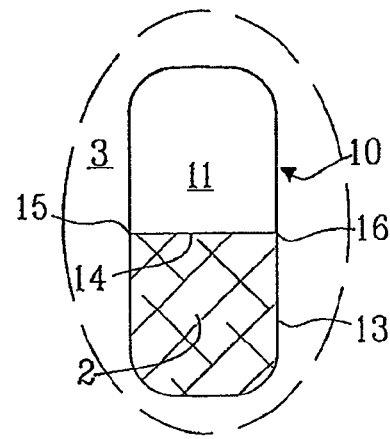
FIG. 1E is an enlarged view of a first invertible flap of the tampon in FIG. 1D.
Figure 1F:
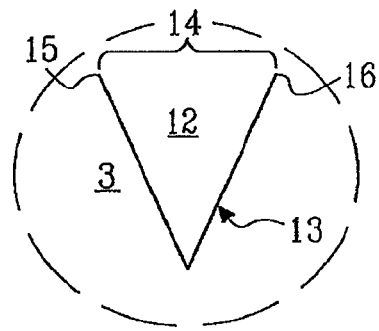
FIG. 1F is an enlarged view of a first invertible flap with an alternative first curve.
Figure 1G:
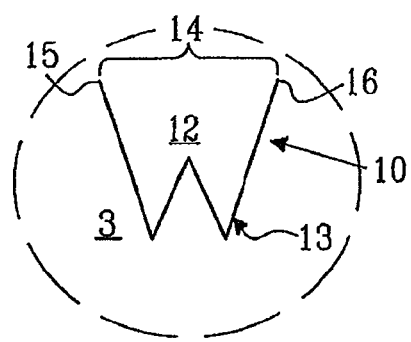
FIG. 1G is an enlarged view of a first invertible flap with an alternative first curve.

Furthermore, in the first embodiment, the shape of the first curve, along which the first slit system 13 extends, is U-shaped. However, the shape of the first curve may be varied, but it may only have such a shape that it contributes to the assurance that the first invertible flap 10 is moved from the first initial position to the first inverted position during withdrawal of the tampon 1. For example, the first curve may be V-shaped (FIG. 1F), square-shaped (not shown), shaped like a toilet lid (not shown), balloon-shaped (not shown) or W-shaped (FIG. 1G).

Furthermore, it is important to ascertain that the first invertible flap 10 is not torn from the cover 3 at the first fold line 14 during withdrawal of the tampon 1 out of the vagina of a user. This may be ascertained by the extension and orientation of the first fold line 14 and the first slit system 13. However, this may also be ascertained by the first fold line 14 being reinforced by being attached to the absorption body 2. For example, the first fold line 14 may be fused or melted together with the absorption body 2. Alternatively, the first fold line 14 may be reinforced by means of an additional strip of material, e.g. cover material or any other surface material, attached over the first fold line 14 on the outer surface 9 of the cover 3.

Furthermore, as described further below, the tampon 1 may in alternatives include one or more additional materials sandwiched between the cover 3 and the absorption body 2. Then the first fold line 14 may be reinforced by being attached to the outermost additional material.

In order to contribute to the assurance that the first invertible flap 10 is moved from the first initial position to the first inverted position during withdrawal of the tampon 1 and in order to contribute to the assurance that the first invertible flap 10 is not torn from the cover 3, the first fold line 14 may be at least 1 mm, preferably at least 2 mm, most preferably at least 3 mm. In addition, in order to obtain the below described spacing effect, the first invertible flap 10 may have an area of at least 1 mm$^2$, preferably at least 4 mm$^2$, most preferably at least 9 mm$^2$ in a plane state. The first invertible flap 10 may have the size of a cilia.

Thus, in accordance with the above, the first embodiment of the tampon 1 shown in FIGS. 1A-E is delivered to a user with all first invertible flaps 10 being positioned in the first initial position. During insertion of the tampon 1 into the vagina of a user and in the insertion state, the first invertible flaps 10 are kept in the first initial position due to their orientation. However, when withdrawing the tampon 1 after use, the first invertible flaps 10 will be moved from the first initial position to the first inverted position by inverting or peeling away from the absorption body 2.

More specifically, when extricating the tampon 1 after use, the user pulls at one or both of the withdrawal strings 6. The pulling action causes the tampon 1 to move in the direction of the applied force. Since the friction between the first inner surfaces 11 of the first invertible flaps 10 and the absorption body 2 is less than the friction between the first outer surfaces 12 of the first invertible flaps 10 and the user's vaginal wall, the first outer surfaces 12 of the first invertible flaps 10 will cling to the vaginal wall. Thereby, the pulling force will also cause the first invertible flaps 10 to gradually invert during withdrawal of the tampon 1. Finally, the first invertible flaps 10 are completely inverted as shown in FIGS. 1D-E.

During inversion and after being completely inverted, the first invertible flaps 10 will act as spacing means, creating a distance between the mucous membranes on the user's vaginal wall and the remainder of the cover 3. In this manner, the first invertible flaps 10 act as removal aids, greatly facilitating the withdrawal of the tampon 1 and minimising the risk of causing abrasion, chafing or other friction-induced discomforts that may otherwise arise when a tampon is being withdrawn. Thus, by means of the first invertible flaps 10, the tampon 1 may be easily and comfortably withdrawn from the vagina even when only partially saturated with menstrual fluid.

Furthermore, as mentioned above, the inner surface 8 and the outer surface 9 of the cover 3 may have different friction characteristics. In case the inner surface 8 is smoother than the outer surface 9, the first inner surface 11 of the first invertible flaps 10 is smoother than the first outer surface 12 of the first invertible flaps 10. The differing friction characteristics contribute to the inversion of the first invertible flaps 10 during withdrawal of the tampon 1 out of the vagina of a user. In addition, the differing friction characteristics imply that after inversion, the smoother first inner surface 11 will be in contact with the user's vaginal wall instead of the first outer surface 12, whereby the friction between the tampon 1 and the user's vaginal wall will be reduced and further withdrawal will be facilitated.

In the first embodiment shown in FIGS. 1A-E, all first invertible flaps 10 of the plurality of first invertible flaps 10 are similar. However, all first invertible flaps 10 of the plurality of first invertible flaps 10 need not be similar, but one or more first invertible flaps 10 may differ from one or more other first invertible flaps 10 by being varied in accordance with one or more of the above described variations. In alternatives, the first curve of one or more of the first invertible flaps 10 of the plurality of first invertible flaps 10 may have another shape than the first curve of one or more other first invertible flaps 10 of the plurality of first invertible flaps 10. For example, the first curve of one or more first invertible flaps 10 may be V-shaped, whereas the first curve of one or more other first invertible flaps 10 may be U-shaped. Thus, the first curve of at least one first invertible flap 10 of the plurality of first invertible flaps 10 may be V-shaped and/or the first curve of at least one first invertible flap 10 of the plurality of first invertible flaps 10 may be U-shaped. However, all first curves may only have such a shape that they contribute to the assurance that the first invertible flaps 10 are moved from the first initial position to the first inverted position during withdrawal of the tampon 1. In further alternatives, the first fold line 14 of one or more of the first invertible flaps 10 of the plurality of first invertible flaps 10 may have a different length and/or a different orientation than the first fold line 14 of one or more other first invertible flaps 10 of the plurality of first invertible flaps 10. For example, the first fold line 14 of one or more first invertible flaps 10 may extend in a direction at least essentially orthogonal to the longitudinal direction (L) of the tampon 1, whereas the first fold line 14 of one or more other first invertible flaps 10 may extend in any other direction. Thus, the first fold line 14 of at least one first invertible flap 10 of the plurality of first invertible flaps 10 may extend in a direction at least essentially orthogonal to the longitudinal direction of the tampon 1. However, all first fold lines 14 extend in such a direction that they contribute to the assurance that the first invertible flaps 10 are moved from the first initial position to the first inverted position during withdrawal of the tampon 1. In still further alternatives, one or more of the first invertible flaps 10 of the plurality of first invertible flaps 10 may have a different area (size) than one or more other first invertible flaps 10 of the plurality of first invertible flaps 10. In case the cover 3 includes first invertible flaps 10 having different areas (sizes), the smaller first invertible flaps 10 may be completely inverted prior to the larger first invertible flaps 10. Thereby, first invertible flaps 10 of different sizes may aid withdrawal to different degrees at different stages of the withdrawal. Furthermore, the first fold line 14 of one, some or all first invertible flaps 10 may be reinforced in accordance with the above. Thus, the first fold line 14 of at least one first invertible flap 10 of the plurality of first invertible flaps 10 may be reinforced in accordance with the above. However, in all alternatives, all first invertible flaps 10 are designed such that they are arranged to be moved between the first initial position and the first inverted position during withdrawal of the tampon 1 so as to aid the withdrawal.

In order to further reduce the friction between the tampon 1 and the vaginal wall during withdrawal of the tampon 1 so as to further aid the withdrawal of the tampon 1, one or more lubricating agents may be provided on at least parts of the first inner surface 11 of one or more of the first invertible flaps 10. Thus, the first inner surface 11 of at least one first invertible flap 10 of the plurality of first invertible flaps 10 may be at least partly provided with at least one lubricating agent. The lubricating agent may be selected from the group consisting of: pectin, hyaluronic acids, glycerides, waxes such as silicone waxes, plant waxes and paraffin wax, and polyvinyl alcohol. However, these are only a few examples of a large variety of substances that may be used as lubricating agents. Different lubricating agents may be provided on different first invertible flaps 10.

As mentioned above, when the tampon 1 is extricated, the first invertible flaps 10 will become inverted such that the first inner surface 11 of all first invertible flaps 10 faces away from the absorption body 2. This implies that the first inner surface 11 of all first invertible flaps 10 will become exposed to the user's vaginal wall. Lubricating agent(s) on any or all of the first inner surfaces 11 will then come in contact with the user's vaginal wall. Thereby, withdrawal of the tampon 1 will be facilitated and some lubrication of the mucous membranes in the vagina will be provided, thus facilitating insertion of a new tampon.

Figure 1H:
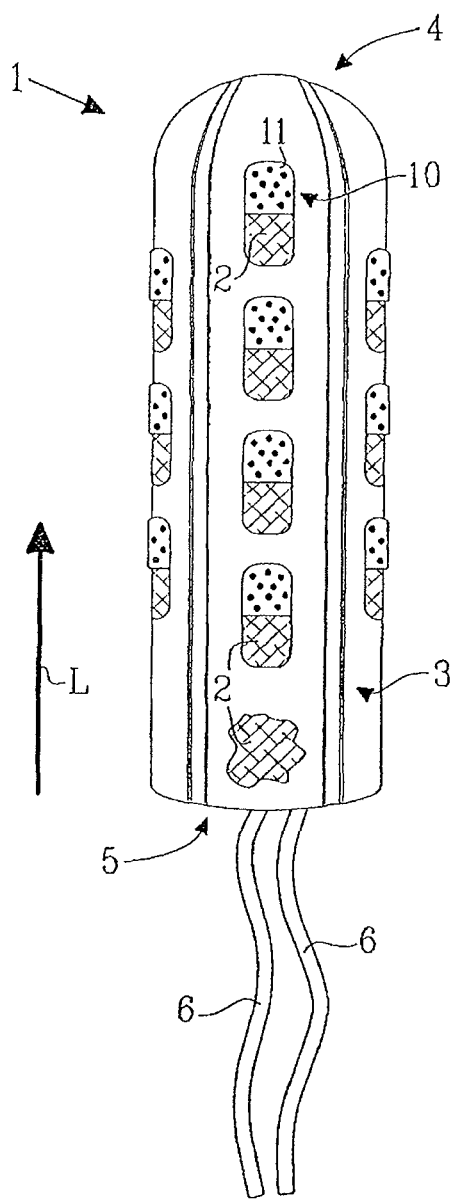
FIG. 1H corresponds to FIG. 1D but with a lubricating agent on the first inner surfaces of the first invertible flaps.

FIG. 1H shows the first embodiment of the tampon 1 shown in FIG. 1D, but with a lubricating agent provided on the first inner surface 11 of all first invertible flaps 10. The lubricating agent is schematically illustrated with dots in FIG. 1H.

By positioning one or more lubricating agents on the first inner surface 11 of one or more first invertible flaps 10, a controlled release of the lubricating agent(s) may be achieved. The lubricating agent(s) is/are released during withdrawal of the tampon 1 when the first invertible flaps 10 are inverted. However, the lubricating agent(s) may also migrate through the cover 3 to the vaginal wall during use of the tampon 1 (i.e. when the tampon 1 is in the inserted state). The migration may be activated by e.g. heat and/or humidity. In addition, the above mentioned fact that lubricating agents may easily migrate onto and/or into a packaging enclosing the tampon when the lubricating agents are positioned on the outer surface of the tampon is substantially avoided. Furthermore, the above mentioned complications in the production process associated with the positioning of the lubricating agents on the outer surface of the tampon are also substantially avoided.

The lubricating agent(s) may be contained in microcapsules. Microencapsulation is used for a variety of personal care applications and the technology currently permits the encapsulation of both water-soluble and water-insoluble material. Typically, microcapsules are made using silica or cellulose. The microcapsules may be constructed such that the lubricating agent(s) is/are encapsulated in the microcapsules until the tampon is withdrawn and the encapsulation broken by tensile forces and/or frictional forces. Alternatively, the encapsulation may be broken by heat and/or humidity.

It is also possible to provide one or more active agents other than lubricating agents on at least parts of the first inner surface 11 of one or more of the first invertible flaps 10. Thus, the first inner surface 11 of at least one first invertible flap 10 of the plurality of first invertible flaps 10 may be at least partly provided with at least one active agent. The active agents may be selected from the group consisting of: odour controlling agents, perfumes, lactic acid producing organisms, pain control agents, sedatives and mixtures thereof. In the case of perfumes or odour control agents, the effect may be advantageous for the user as well as for prohibiting unwanted odour from the used and discarded tampon. By positioning one or more active agents on the first inner surface 11 of one or more first invertible flaps 10, it is possible to obtain a controlled release of the active agent(s). The active agent(s) is/are released during withdrawal when the first invertible flaps 10 are inverted. The active agent(s) may be encapsulated until the tampon is withdrawn and the encapsulation broken by tensile forces and/or frictional forces. Alternatively, the encapsulation may be broken by humidity and/or heat.

The lubricating agent(s) and/or the active agent(s) may be provided on the first inner surface 11 of one or more first invertible flaps 10 due to the fact that the inner surface 8 of the cover 3 is completely or partly provided with the lubricating agent(s) and/or the active agent(s) or due to the fact that the outer surface of the absorbent body 2 is completely or partly provided with the lubricating agent(s) and/or the active agent(s). In case the tampon 1 includes one or more additional materials sandwiched between the cover 3 and the absorption body 2, the lubricating agent(s) and/or the active agent(s) may be provided on the first inner surface 11 of one or more first invertible flaps 10 due to the fact that the outermost additional layer is provided with the lubricating agent(s) and/or the active agent(s). Thus, lubricating agent(s) and/or the active agent(s) may be positioned between the cover 3 and the absorption body 2 or between the cover 3 and an additional material covering the absorption body 2.

Figure 1I:
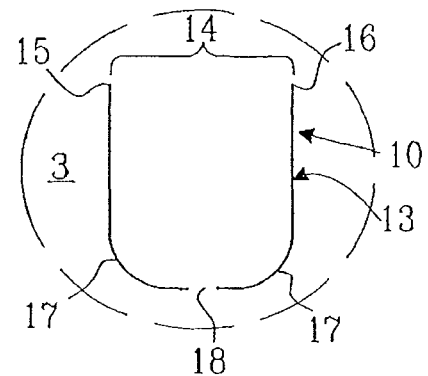
FIG. 1I is an enlarged view of a first invertible flap with an alternative first slit system.

Furthermore, the first embodiment or any of the alternatives described above may be varied in that the first slit system 13 of at least one first invertible flap 10 is constituted by more than one slit. For example, the first slit system 13 of at least one first invertible flap 10 of the plurality of first invertible flaps 10 may be constituted by two first slits 17 and a first interruption 18 between the two first slits 17 (FIG. 1I). Then each of the two first slits 17 and the first interruption 18 extends along respective parts of the respective first curve. The first interruption 18 is constituted by a non-slitted portion of the cover 3 and is arranged to be broken during withdrawal of the tampon 1 out of the vagina of a user so as to enable folding of the respective first invertible flap 10 around the first fold line 14. By means of the first interruption 18 the respective first invertible flap 10 is securely kept in the first initial position before use of the tampon 1. Alternatively, the first slit system 13 of at least one first invertible flap 10 may be constituted by more than two first slits, whereby one first interruption is positioned between each pair of consecutive first slits (not shown). Then each first slit and first interruption extends along a respective part of the respective first curve, and each first interruption is constituted by a non-slitted portion according to the above. Thus, the first slit system 13 of at least one first invertible flap 10 of the plurality of first invertible flaps 10 may be constituted by at least two first slits and a first interruption between each pair of consecutive first slits, whereby each first slit and each first interruption extends along a respective part of the respective first curve and whereby each first interruption is constituted by a non-slitted portion of the cover according to the above.

Figure 1J:
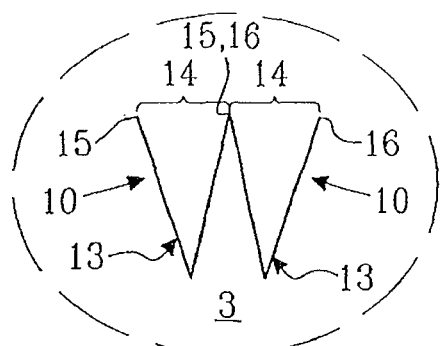
FIG. 1J is an enlarged view of two first invertible flaps having a common point.

In addition, as shown in FIG. 1J, the first end point 16 of the first slit system 13 of one first invertible flap 10 may also constitute the first start point 15 of the first slit system 13 of another first invertible flap 10.

Figure 1K:
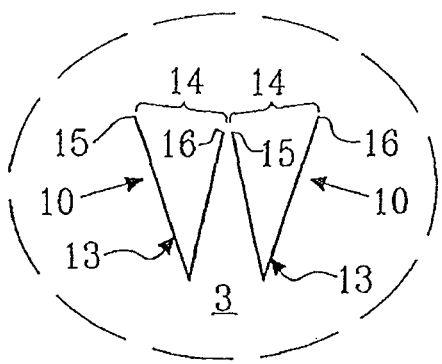
FIG. 1K is an enlarged view of two first invertible flaps with different orientations of the first fold lines.

Furthermore, as mentioned above, the first fold line 14 of the first invertible flap 10 may extend in any direction in which it contributes to the assurance that the first invertible flap 10 is moved from the first initial position to the first inverted position during withdrawal of the tampon 1. In addition, the first fold line 14 of different first invertible flaps 10 may extend in different directions. One such example is shown in FIG. 1K.

Figures 2A, 2B:
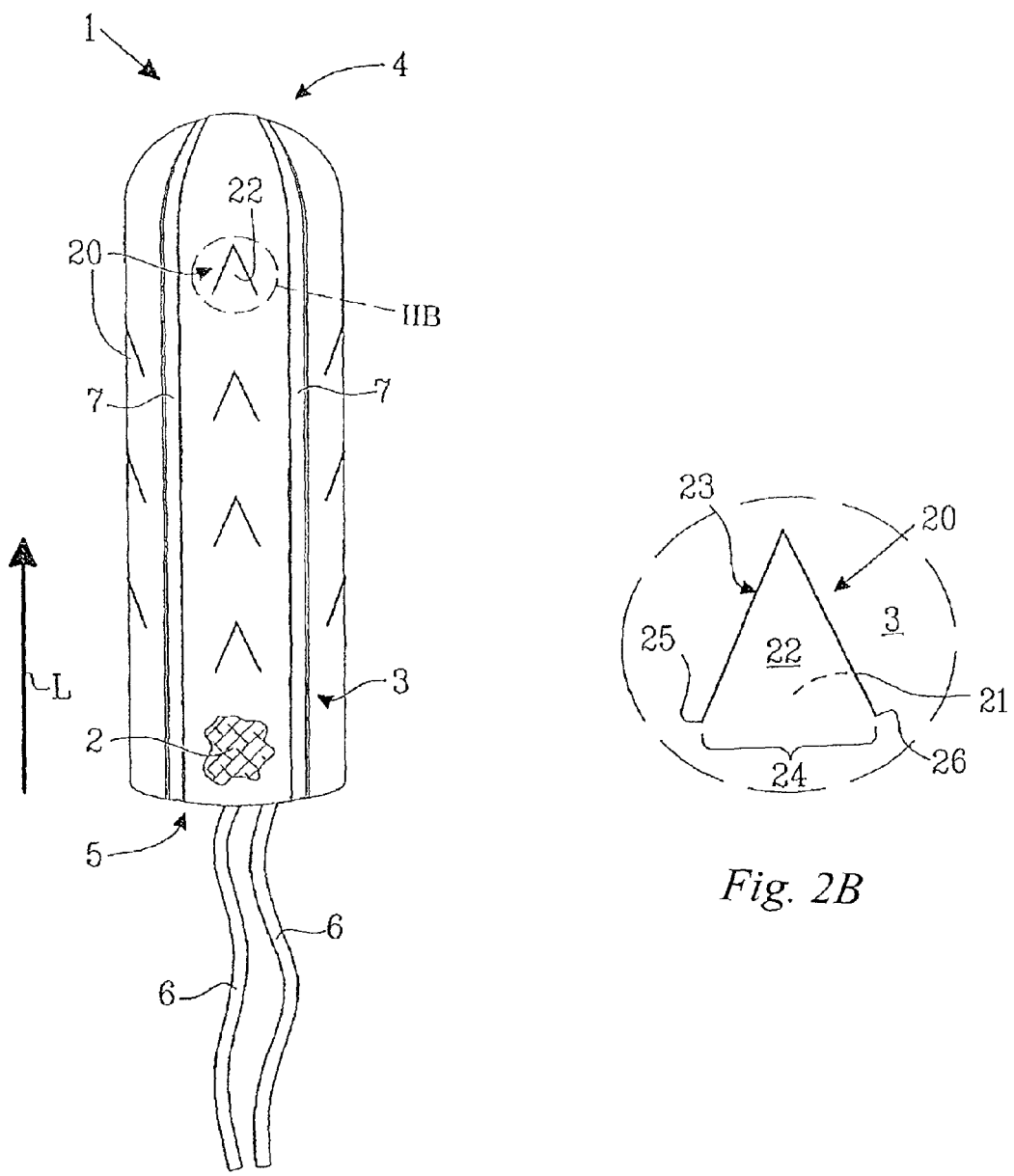
FIG. 2A is a side view of a second embodiment of a tampon when the second invertible flaps are positioned in a second initial position.
FIG. 2B is an enlarged view of a second invertible flap of the tampon in FIG. 2A.

FIG. 2A shows a second embodiment of the tampon 1. The second embodiment of the tampon 1 corresponds to the first embodiment shown in FIGS. 1A-E except for concerning the first invertible flaps 10. The second embodiment of the tampon 1 does not include the first invertible flaps 10, but includes instead a plurality of second invertible flaps 20.

More specifically, in the second embodiment shown in FIG. 2A, the liquid permeable cover 3 includes a plurality of second invertible flaps 20. All second invertible flaps 20 are similar in the second embodiment and FIG. 2B shows an enlarged view of one second invertible flap 20 of the plurality of second invertible flaps 20. In the following, one of the second invertible flaps 20 of the second embodiment will be described with reference to FIGS. 2A-B.

The second invertible flap 20 is constituted by a portion of the cover 3 (i.e. the second invertible flap 20 is formed by a part of the cover 3) and includes a second inner surface 21 and an opposite second outer surface 22. The second inner surface 21 of the second invertible flap 20 constitutes a part of the inner surface 8 of the cover 3 and the second outer surface 22 constitutes a part of the outer surface 9 of the cover 3.

The second invertible flap 20 is partly detached from the remainder of the cover 3, i.e. one or more border parts of the first invertible flap 20 are detached from (non-connected with) the remainder of the cover 3. The detachment is obtained by means of a second slit system 23 provided in the cover 3. However, the second invertible flap 20 is connected with the remainder of the cover 3 via a second fold line 24. Thus, the second invertible flap 20 is delimited by the second fold line 24 and the second slit system 23, i.e. the second invertible flap 20 is completely surrounded by the second fold line 24 and the second slit system 23.

More specifically, the second fold line 24 extends along a line between a second start point 25 and a second end point 26. Furthermore, the second slit system 23 extends along a second curve starting from the second start point 25 and ending in the second end point 26. In the second embodiment shown in FIGS. 2A-B, the second slit system 23 is constituted by one slit extending from the second start point 25 to the second end point 26 along the second curve. The second curve bulges away from the second fold line 24 towards the insertion end 4. In the second embodiment, the second curve is V-shaped. Thereby, the slit constituting the second slit system 23 is also V-shaped. The second curve may alternatively have any other suitable shape. This will be further described below.

The second slit system 23 and the second fold line 24 delimiting the second invertible flap 20 are provided such that the second invertible flap 20 is arranged to be moved between a second initial position (FIGS. 2A-B) and a second inverted position (FIGS. 2C-D) during insertion of the tampon 1 into the vagina of a user so as to aid the insertion. More specifically, the second slit system 23 and the second fold line 24 delimiting the second invertible flap 20 have such an extension and orientation that the second invertible flap 20 is arranged to be moved between a second initial position and a second inverted position during insertion of the tampon 1 into the vagina of a user. Thus, the second invertible flap 20 is shaped and oriented by means of the second slit system 23 and the second fold line 24 such that the second invertible flap 20 is arranged to be moved between a second initial position and a second inverted position during insertion of the tampon 1 into the vagina of a user. The second invertible flap 20 is arranged to be moved between the second initial position and the second inverted position by being folded around the second fold line 24.

The second invertible flap 20 is positioned in the second initial position before use of the tampon 1 (FIGS. 2A-B). In the second initial position, the second inner surface 21 of the second invertible flap 20 faces the absorption body 2 and the second outer surface 22 of the second invertible flap 20 faces away from the absorption body 2. However, the second invertible flap 20 is arranged to be moved to the second inverted position (FIGS. 2C-D) during insertion of the tampon 1 into the vagina of a user. In the second inverted position, the second inner surface 21 of the second invertible flap 20 faces away from the absorption body 2 and the second outer surface 22 of the second invertible flap 20 faces the absorption body 2. Thus, in the second inverted position, the second outer surface 22 of the second invertible flap 20 is at least partly in contact with the outer surface 9 of the cover 3 and an opening corresponding to the shape of the second invertible flap 20 is formed in the cover 3, whereby the absorption body 2 is exposed by means of the opening.

In accordance with the above, the slit of the second slit system 23 of the second embodiment includes two interfaces. The two interfaces may be in contact with each other in the second initial position. However, the two interfaces may alternatively not be in contact, or only be partly in contact, with each other in the second initial position due to the fact that the produced second invertible flap 20 or parts thereof is/are moved slightly outwards from the remainder of the cover 3 and/or due to the fact that the free edges of the produced second invertible flap 20 are bent away from the remainder of the cover 3 by means of the utilized method and/or tool for providing the second slit system 23. The expression that "the second inner surface faces the absorption body in the second initial position" is herein intended to include that the complete second inner surface faces the absorption body, or that the main part of the second inner surface faces the absorption body but that one or more free edge portions of the second invertible flap is/are bent away from the remainder of the cover due to influences by the production method and/or tool. Furthermore, in case the second invertible flap or parts thereof is/are moved slightly outwards from the remainder of the cover due to the production method and/or tool, the second inner surface is regarded as facing the absorption body.

As mentioned above, the second slit system 23 and the second fold line 24 delimiting the second invertible flap 20 have such an extension and orientation that the second invertible flap 20 is arranged to be moved between a second initial position and a second inverted position during insertion of the tampon 1 into the vagina of a user. In particular embodiments, as shown in FIGS. 2A-D, the second fold line 24 extends in a direction orthogonal, or at least essentially orthogonal, to the longitudinal direction L of the tampon 1 in order to contribute to the assurance that the second invertible flap 20 is moved from the second initial position to the second inverted position during insertion of the tampon 1. However, the direction in which the second fold line 24 extends may be varied, but it may only be varied to extend in such a direction that it contributes to the assurance that the second invertible flap 20 is moved from the second initial position to the second inverted position during insertion of the tampon 1.

Furthermore, in the second embodiment, the shape of the second curve, along which the second slit system 23 extends, is V-shaped. However, the shape of the second curve may be varied, but it may only have such a shape that it contributes to the assurance that the second invertible flap 20 is moved from the second initial position to the second inverted position during insertion of the tampon 1. For example, the second curve may be U-shaped (FIG. 2E), square-shaped (not shown), shaped like a toilet lid (not shown), balloon-shaped (not shown) or W-shaped.

Furthermore, it is important to ascertain that the second invertible flap 20 is not torn from the cover 3 at the second fold line 24 during insertion of the tampon 1 into the vagina of a user. This may be ascertained by the extension and orientation of the second fold line 24 and the second slit system 23. However, this may also be ascertained by the second fold line 24 being reinforced by being attached to the absorption body 2. For example, the second fold line 24 may be fused or melted together with the absorption body 2. Alternatively, the second fold line 24 may be reinforced by means of an additional strip of material, e.g. cover material or any other surface material, attached over the second fold line 24 on the outer surface 9 of the cover 3. Furthermore, as described further below, the tampon 1 may in alternatives include one or more additional materials sandwiched between the cover 3 and the absorption body 2. Then the second fold line 24 may be reinforced by being attached to the outermost additional material.

In order to contribute to the assurance that the second invertible flap 20 is moved from the second initial position to the second inverted position during insertion of the tampon 1 and in order to contribute to the assurance that the second invertible flap 20 is not torn from the cover 3, the second fold line 24 may be at least 1 mm, preferably at least 2 mm, most preferably at least 3 mm. In addition, in order to obtain the below described spacing effect, the second invertible flap 20 may have an area of at least 1 $mm^2$, preferably at least 4 $mm^2$, most preferably at least 9 $mm^2$ in a plane state. The second invertible flap 20 may have the size of a cilia.

Thus, in accordance with the above, the second embodiment of the tampon 1 shown in FIGS. 2A-D is delivered to a user with all second invertible flaps 20 being positioned in the second initial position. During insertion of the tampon 1 into the vagina of a user, the second invertible flaps 20 will be moved from the second initial position to the second inverted position by inverting or peeling away from the absorption body 2.

Figure 2C:
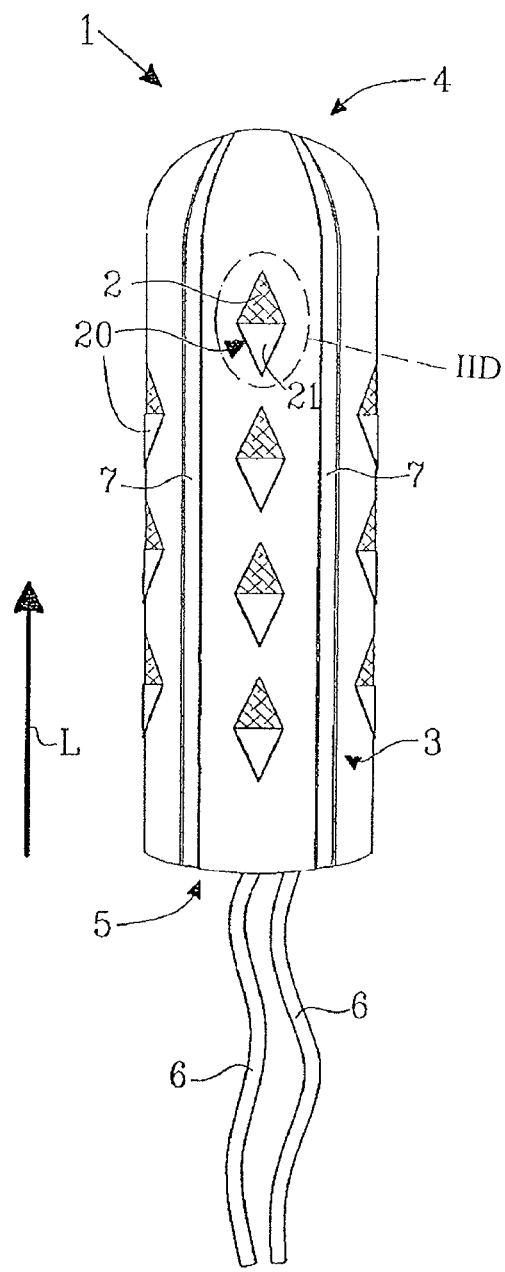
FIG. 2C is a side view of the second embodiment of the tampon when the second invertible flaps are positioned in a second inverted position.
Figure 2D:
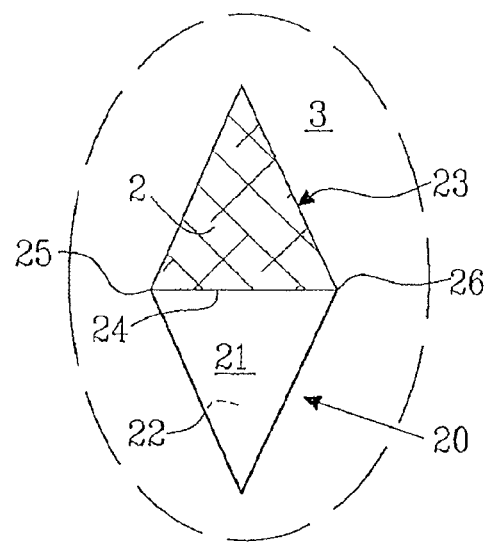
FIG. 2D is an enlarged view of a second invertible flap of the tampon in FIG. 2C.
Figure 2E:
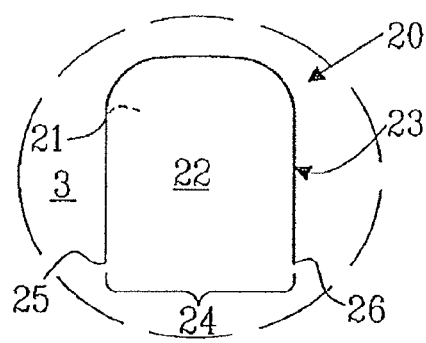
FIG. 2E is an enlarged view of a second invertible flap with an alternative second curve.

More specifically, when inserting the tampon 1, the tampon 1 is pushed into the vagina. The pushing action causes the tampon 1 to move in the direction of the applied force. Since the friction between the second inner surfaces 21 of the second invertible flaps 20 and the absorption body 2 is less than the friction between the second outer surfaces 22 of the second invertible flaps 20 and the user's vaginal wall, the second outer surfaces 22 of the second invertible flaps 20 will cling to the vaginal wall. Thereby, the pushing force will also cause the second invertible flaps 20 to gradually invert during insertion of the tampon 1. Finally, the second invertible flaps 20 are completely inverted as shown in FIGS. 2C-D.

During inversion and after being completely inverted, the second invertible flaps 20 will act as spacing means, creating a distance between the mucous membranes on the user's vaginal wall and the remainder of the cover 3. In this manner, the second invertible flaps 20 act as insertion aids, further facilitating the insertion of the tampon 1 and minimising the risk of causing abrasion, chafing or other friction-induced discomforts that may otherwise arise when a tampon is being inserted. As mentioned above, dried-out mucous membranes make it difficult and uncomfortable to insert a new tampon to replace another tampon that has been removed. Thus, by means of the second invertible flaps 20, the tampon 1 may easily and comfortably be inserted into the vagina of a user.

Furthermore, as mentioned above the inner surface 8 and the outer surface 9 of the cover 3 may have different friction characteristics. In case the inner surface 8 is smoother than the outer surface 9, the second inner surface 21 of the second invertible flaps 20 is smoother than the second outer surface 22 of the second invertible flaps 20. The differing friction characteristics contribute to the inversion of the second invertible flaps 20 during insertion of the tampon 1 into the vagina of a user. In addition, the differing friction characteristics imply that after inversion, the smoother second inner surface 21 will be in contact with the user's vaginal wall instead of the second outer surface 22, whereby the friction between the tampon 1 and the user's vaginal wall will be reduced and further insertion will be facilitated.

In the second embodiment shown in FIGS. 2A-D, all second invertible flaps 20 of the plurality of second invertible flaps 20 are similar. However, all second invertible flaps 20 of the plurality of second invertible flaps 20 need not be similar, but one or more second invertible flaps 20 may differ from one or more other second invertible flaps 20 by being varied in accordance with one or more of the above described variations. In alternatives, the second curve of one or more of the second invertible flaps 20 of the plurality of second invertible flaps 20 may have another shape than the second curve of one or more other second invertible flaps 20 of the plurality of second invertible flaps 20. For example, the second curve of one or more second invertible flaps 20 may be V-shaped, whereas the second curve of one or more other second invertible flaps 20 may be U-shaped. Thus, the second curve of at least one second invertible flap 20 of the plurality of second invertible flaps 20 may be V-shaped and/or the second curve of at least one second invertible flap 20 of the plurality of second invertible flaps 20 may be U-shaped. However, all second curves may only have such a shape that they contribute to the assurance that the second invertible flaps 20 are moved from the second initial position to the second inverted position during insertion of the tampon 1. In further alternatives, the second fold line 24 of one or more of the second invertible flaps 20 of the plurality of second invertible flaps 20 may have a different length and/or a different orientation than the second fold line 24 of one or more other second invertible flaps 20 of the plurality of second invertible flaps 20. For example, the second fold line 24 of one or more second invertible flaps 20 may extend in a direction at least essentially orthogonal to the longitudinal direction (L) of the tampon 1, whereas the second fold line 24 of one or more other second invertible flaps 20 may extend in any other direction. Thus, the second fold line 24 of at least one second invertible flap 20 of the plurality of second invertible flaps 20 may extend in a direction at least essentially orthogonal to the longitudinal direction of the tampon 1. However, all second fold lines 24 extend in such a direction that they contribute to the assurance that the second invertible flaps 20 are moved from the second initial position to the second inverted position during insertion of the tampon 1. In still further alternatives, one or more of the second invertible flaps 20 of the plurality of second invertible flaps 20 may have a different area (size) than one or more other second invertible flaps 20 of the plurality of second invertible flaps 20. In case the cover 3 includes second invertible flaps 20 having different areas (sizes), second invertible flaps 20 of different sizes may aid insertion of the tampon 1 to different degrees at different stages of the insertion. Furthermore, the second fold line 24 of one, some or all second invertible flaps 20 may be reinforced in accordance with the above. Thus, the second fold line 24 of at least one second invertible flap 20 may be reinforced in accordance with the above. However, in all alternatives, all second invertible flaps 20 are designed such that they are arranged to be moved between the second initial position and the second inverted position during insertion of the tampon 1 so as to aid the insertion.

In order to further reduce the friction between the tampon 1 and the vaginal wall during insertion of the tampon 1 so as to further aid the insertion of the tampon 1, one or more lubricating agents may be provided on at least parts of the second inner surface 21 of one or more of the second invertible flaps 20. Thus, the second inner surface 21 of at least one second invertible flap 20 of the plurality of second invertible flaps 20 may be at least partly provided with at least one lubricating agent. The lubricating agent may be selected from the group consisting of: pectin, hyaluronic acids, glycerides, waxes such as silicone waxes, plant waxes and paraffin wax, and polyvinyl alcohol. However, these are only a few examples of a large variety of substances that may be used as lubricating agents. Different lubricating agents may be provided on different second invertible flaps 20.

As mentioned above, when the tampon 1 is inserted, the second invertible flaps 20 will become inverted such that the second inner surface 21 of all second invertible flaps 20 faces away from the absorption body 2. This implies that the second inner surface 21 of all second invertible flaps 20 will become exposed to the user's vaginal wall. Lubricating agent(s) on any or all of the second inner surfaces 21 will then come in contact with the user's vaginal wall. Thereby insertion of the tampon 1 will be facilitated and some lubrication of the mucous membranes in the vagina will be provided, thus also facilitating withdrawal of the tampon 1.

Figure 2F:
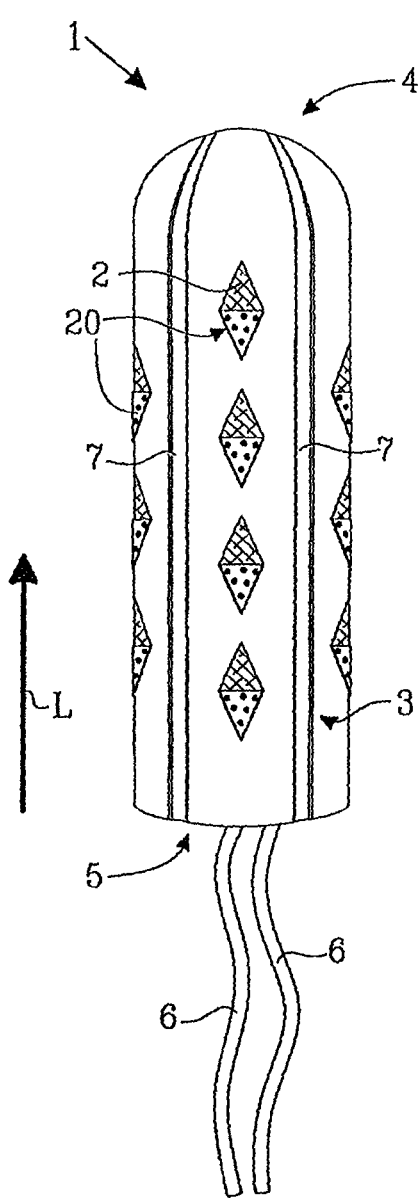
FIG. 2F corresponds to FIG. 2C but with a lubricating agent on the second inner surfaces of the second invertible flaps.

FIG. 2F shows the second embodiment of the tampon 1 shown in FIG. 2C, but with a lubricating agent provided on the second inner surface 21 of all second invertible flaps 20. The lubricating agent is schematically illustrated with dots in FIG. 2F.

The lubricating agent(s) may be contained in microcapsules as described above in association with the first embodiment. The microcapsules may be constructed such that the lubricating agent(s) is/are encapsulated in the microcapsules until the tampon is inserted and the encapsulation broken by tensile forces and/or frictional forces. Alternatively, the encapsulation may be broken by humidity and/or heat.

It is also possible to provide one or more active agents other than lubricating agents on at least parts of the second inner surface 21 of one or more of the second invertible flaps 20. Thus, the second inner surface 21 of at least one second invertible flap 20 of the plurality of second invertible flaps 20 may be at least partly provided with at least one active agent. The active agents may be selected from the group consisting of: odour controlling agents, perfumes, lactic acid producing organisms, pain control agents, sedatives and mixtures thereof. By positioning one or more active agents on the second inner surface 21 of one or more second invertible flaps 20, it is possible to obtain a controlled release of the active agent(s). The active agent(s) is/are released during insertion when the second invertible flaps 20 are inverted. The active agent(s) may be encapsulated until the tampon is inserted and the encapsulation broken by tensile forces and/or frictional forces. Alternatively, the encapsulation may be broken by humidity and/or heat.

The lubricating agent(s) and/or the active agent(s) may be provided on the second inner surface 21 of one or more second invertible flaps 20 due to the fact that the inner surface 8 of the cover 3 is completely or partly provided with the lubricating agent(s) and/or the active agent(s) or due to the fact that the outer surface of the absorbent body 2 is completely or partly provided with the lubricating agent(s) and/or the active agent(s). In case the tampon 1 includes one or more additional materials sandwiched between the cover 3 and the absorption body 2, the lubricating agent(s) and/or the active agent(s) may be provided on the second inner surface 21 of one or more second invertible flaps 20 due to the fact that the outermost additional layer is provided with the lubricating agent(s) and/or the active agent(s).

Figure 2G:
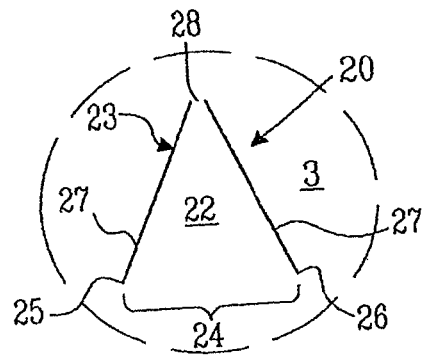
FIG. 2G is an enlarged view of a second invertible flap with an alternative second slit system.

Furthermore, the second embodiment or any of the alternatives described above may be varied in that the second slit system 23 of at least one second invertible flap 20 is constituted by more than one slit. For example, the second slit system 23 of at least one second invertible flap 20 of the plurality of second invertible flaps 20 may be constituted by two second slits 27 and a second interruption 28 between the two second slits 27 (FIG. 2G). Then each of the two second slits 27 and the second interruption 28 extends along respective parts of the respective second curve. The second interruption 28 is constituted by a non-slitted portion of the cover 3 and is arranged to be broken during insertion of the tampon 1 into the vagina of a user so as to enable folding of the respective second invertible flap 20 around the second fold line 24. By means of the second interruption 28 the respective second invertible flap 20 is securely kept in the second initial position before use of the tampon 1. Alternatively, the second slit system 23 of at least one second invertible flap 20 may be constituted by more than two second slits, whereby one second interruption is positioned between each pair of consecutive second slits (not shown). Then each second slit and second interruption extends along a respective part of the respective second curve, and each second interruption is constituted by a non-slitted portion according to the above. Thus, the second slit system 23 of at least one second invertible flap 20 of the plurality of second invertible flaps 20 may be constituted by at least two second slits and a second interruption between each pair of consecutive second slits, whereby each second slit and each second interruption extends along a respective part of the respective second curve and whereby each second interruption is constituted by a non-slitted portion of the cover.

Figure 2H:
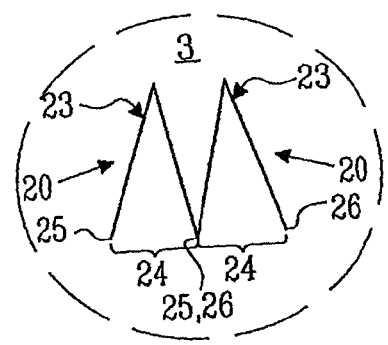
FIG. 2H is an enlarged view of two second invertible flaps having a common point.

In addition, as shown in FIG. 2H, the second end point 26 of the second slit system 23 of one second invertible flap 20 may also constitute the second start point 25 of the second slit system 23 of another second invertible flap 20.

Figure 2I:
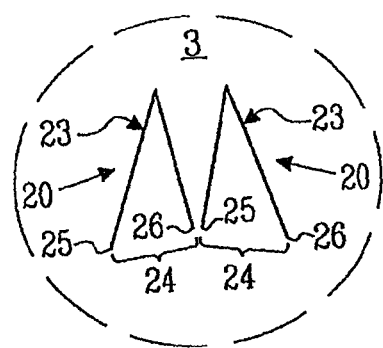
FIG. 2I is an enlarged view of two second invertible flaps with different orientations of the second fold lines.

Furthermore, as mentioned above, the second fold line 24 of the second invertible flap 20 may extend in any direction in which it contributes to the assurance that the second invertible flap 20 is moved from the second initial position to the second inverted position during insertion of the tampon 1. In addition, the second fold line 24 of different second invertible flaps 20 may extend in different directions. One such example is shown in FIG. 2I.

Figure 3:
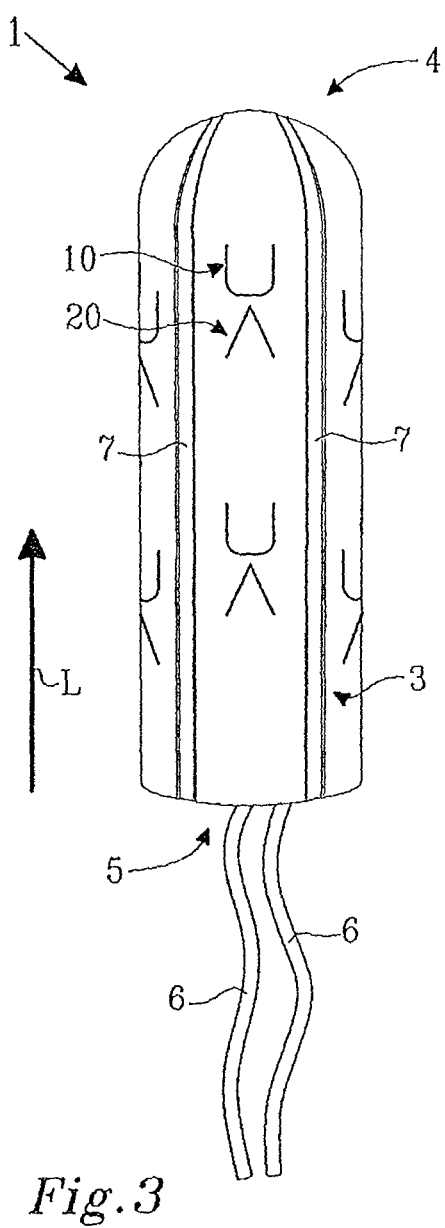
FIG. 3 is a side view of a third embodiment of the tampon.

FIG. 3 shows a third embodiment of the tampon 1. The third embodiment corresponds to the first embodiment shown in FIGS. 1A-E, but includes also a plurality of second invertible flaps 20 according to the second embodiment shown in FIGS. 2A-D. Thus, the third embodiment is a combination of the first and second embodiments.

More specifically, the third embodiment of the tampon 1 includes a plurality of first invertible flaps 10 and a plurality of second invertible flaps 20. In the third embodiment all of the first invertible flaps 10 are similar and correspond to the first invertible flaps 10 of the first embodiment. Likewise, all of the second invertible flaps 20 are similar and correspond to the second invertible flaps 20 of the second embodiment. However, the first invertible flaps 10 may be varied in accordance with the variations described in conjunction with the first embodiment and the second invertible flaps 20 may be varied in accordance with the variations described in conjunction with the second embodiment. For example, the first inner surface 11 of one or more of the first invertible flaps 10 and/or the second inner surface 21 of one or more of the second invertible flaps 20 may be at least partly provided with one or more lubricating agents.

Thus, in accordance with the above, the third embodiment of the tampon 1 shown in FIG. 3 is delivered to a user with all first invertible flaps 10 being positioned in the first initial position and all second invertible flaps 20 being positioned in the second initial position. During insertion of the tampon 1 into the vagina of a user and in the insertion state, the first invertible flaps 10 are kept in the first initial position due to their orientation. However, during insertion of the tampon 1 into the vagina of a user, the second invertible flaps 20 will gradually invert to the second inverted position as shown in FIGS. 2C-D. Furthermore, when withdrawing the tampon 1 after use, the first invertible flaps 10 will gradually invert from the first initial position to the first inverted position as shown in FIGS. 1D-E.

In this manner, the third embodiment of the tampon 1 includes means for both aiding insertion and withdrawal. The second invertible flaps 20 act as insertion aids, further facilitating the insertion of the tampon 1 and minimising the risk of causing abrasion, chafing or other friction-induced discomforts that may otherwise arise when a tampon is being inserted as described above in conjunction with the second embodiment. In addition, the first invertible flaps 10 act as removal aids, greatly facilitating the withdrawal of the tampon 1 and minimising the risk of causing abrasion, chafing or other friction-induced discomforts that may otherwise arise when a tampon is being withdrawn as described above in conjunction with the first embodiment.

Furthermore, the above described embodiments have been shown in the drawings as having first invertible flaps 10 and/or second invertible flaps 20 spread over most of the cover 3. However, the first invertible flaps 10 and/or the second invertible flaps 20 may alternatively be concentrated to only one or more specific parts of the cover 3. For example, the first invertible flaps 10 may be concentrated to a part of the cover 3 in the vicinity of the withdrawal end 5 or to the half of the cover 3 being located nearest the withdrawal end 5 and the second invertible flaps 20 may be concentrated to a part of the cover 3 in the vicinity of the insertion end 4 or to the half of the cover 3 being located nearest the insertion end 4. In addition, the first invertible flaps 10 and/or the second invertible flaps 20 may be positioned in any suitable pattern on the cover 3 or in a random pattern. Furthermore, different parts of the cover 3 may include first invertible flaps 10 having different shapes and/or sizes. For example, first invertible flaps 10 in a part of the cover 3 in the vicinity of the withdrawal end 5 may be smaller than first invertible flaps 10 in a part of the cover 3 in the vicinity of the insertion end 4. Likewise, different parts of the cover 3 may include second invertible flaps 20 having different shapes and/or sizes. For example, second invertible flaps 20 in a part of the cover 3 in the vicinity of the insertion end 4 may be smaller than second invertible flaps 20 in a part of the cover 3 in the vicinity of the withdrawal end 5.

In addition, in the above described embodiments, the tampon 1 includes only one cover, i.e. the cover 3. However, one or more additional layers of cover material or any other material could be sandwiched between the cover 3 and the absorption body 2. In case one or more additional material layers is/are sandwiched between the cover 3 and the absorption body 2, the absorption body 2 is not exposed when the first invertible flaps 10 or the second invertible flaps 20 are positioned in the first inverted position and the second inverted position, respectively, but the outermost additional layer is then exposed.

According to the above, the tampon 1 may include a plurality of first invertible flaps 10 and/or a plurality of second invertible flaps 20. The phrase "a plurality of flaps" is herein intended to mean two or more flaps The tampon 1 may be constructed by any conventional method. For example, the tampon 1 may be manufactured by compressing a mass of absorbent fibres to form the absorption body 2 and thereafter surrounding the absorption body 2 with the cover material. Alternatively, the tampon 1 may be constructed by positioning a layer of absorbent material on a layer of cover material and then rolling the two layers into a roll. This uncompressed roll is known as a "softwind". The softwind is then compressed such that the tampon is formed. It is also possible to first roll a layer of the absorbent material into a roll and then wrap a layer of the cover material around it. The roll is thereafter compressed. In addition, it is also possible to roll up and compress a layer of absorbent material before wrapping it in the layer of cover material. Alternatively, the absorption body may be formed by crossing two absorption elements on each other and drawing a string through the absorption elements, where after the absorption elements are gathered together by means of pulling the string. Still alternatively, the absorbent material may be filled in a bag, which then is compressed. The first slit systems 13 and the second slit systems 23 can be formed in the cover 3 before application of the cover 3 around the absorption body 2. However, they may also be formed in the cover 3 after application of the cover 3 around the absorption body 2 by means of e.g. laser technique.

The tampon 1 may be a digital (non-applicator) tampon or an applicator tampon. Embodiments including second invertible flaps 20 are especially advantageous to provide as digital tampons. Embodiments including first invertible flaps 10 are advantageous to provide as digital tampons or as applicator tampons.

The invention has been described with reference to the embodied figures. However, the invention is not limited to the above-described embodiments and alternatives alone. Features from one or more of the above embodiments and alternatives may be combined as required, and the ultimate scope of the invention should be understood as being defined in the appended claims.

The invention claimed is:

1. A tampon comprising:
    an elongated absorption body at least partly enclosed in a liquid permeable cover,
    an insertion end,
    a withdrawal end, and
    at least one withdrawal string extending from said withdrawal end,
    wherein said liquid permeable cover comprises a plurality of first invertible flaps or a plurality of second invertible flaps or a combination thereof,
    wherein at least one first invertible flap of said plurality of first invertible flaps is constituted by a portion of said cover and comprises a first inner surface and an opposite first outer surface, said at least one first invertible flap is partly detachable from the remainder of said cover by a first slit system provided in said cover, is connected with the remainder of said cover via a first fold line, and is delimited by said first fold line and said first slit system,
    wherein said first fold line extends along a line between a first start point and a first end point of said first slit system,
    wherein said first slit system comprises at least one slit and extends along a first curve starting from said first start point and ending in said first end point, said first curve bulging away from said first fold line towards said withdrawal end,
    wherein said first slit system and said first fold line are arranged such that said at least one first invertible flap is movable between a first initial position and a first inverted position during withdrawal of said tampon out of the vagina of a user so as to aid said withdrawal, by being folded around said first fold line, and
    wherein said at least one first invertible flap is positioned in said first initial position before use of said tampon, and said first inner surface faces said absorption body in said first initial position and faces away from said absorption body in said first inverted position, and
    wherein said at least one second invertible flap is constituted by a portion of said cover and comprises a second inner surface and an opposite second outer surface, said at least one second invertible flap is partly detached from the remainder of said cover by a second slit system provided in said cover, is connected with the remainder of said cover via a second fold line, and is delimited by said second fold line and said second slit system,
    wherein said second fold line extends along a line between a second start point and a second end point of said second slit system,
    wherein said second slit system comprises at least one slit and extends along a second curve starting from said second start point and ending in said second end point, said second curve bulging away from said second fold line towards said insertion end,
    wherein said second slit system and said second fold line are arranged such that said at least one second invertible flap is movable between a second initial position and a second inverted position during insertion of said tampon into the vagina of a user so as to aid said insertion by being folded around said second fold line, and
    wherein said at least one second invertible flap is positioned in said second initial position before use of said tampon, and said second inner surface faces said absorption body in said second initial position and faces away from said absorption body in said second inverted position.

2. The tampon according to claim 1, wherein the first inner surface of said at least one first invertible flap is at least partly provided with at least one lubricating agent.

3. The tampon according to claim 2, wherein said lubricating agent is selected from the group consisting of:
    pectin, hyaluronic acids, glycerides, and polyvinyl alcohol.

4. The tampon according to claim 1, wherein the first inner surface of said at least one first invertible flap is at least partly provided with at least one active agent selected from the group consisting of: odour controlling agents, perfumes, lactic acid producing organisms, pain control agents, and sedatives and mixtures thereof.

5. The tampon according to claim 1 wherein the first slit system of said at least one first invertible flap is constituted by one slit extending from said first start point to said first end point along said first curve.

6. The tampon according to claim 1 wherein the first slit system of said at least one first invertible flap is constituted by at least two first slits and a first interruption between each pair of consecutive first slits, wherein each first slit and each first interruption extends along a respective part of the respective first curve, wherein each first interruption is constituted by a non-slitted portion of said cover, and wherein each first interruption is arranged to be broken during withdrawal of said tampon out of the vagina of a user so as to enable folding of said first invertible flap around said first fold line.

7. The tampon according to claim 1, wherein the first curve of said at least one first invertible flap has another shape than a first curve of one or more other first invertible flaps of said plurality of first invertible flaps.

8. The tampon according to claim 1, wherein the first curve of said at least one first invertible flap is V-shaped.

9. The tampon according to claim 1, wherein the first curve of said at least one first invertible flap is U-shaped.

10. The tampon according to claim 1, wherein the first fold line of said at least one of the first invertible flap has at least a different length or a different orientation than a first fold line of one or more other first invertible flaps of said plurality of first invertible flaps.

11. The tampon according to claim 1, wherein the first fold line of said at least one first invertible flap extends in a direction at least essentially orthogonal to the longitudinal direction of said tampon.

12. The tampon according to claim 1, wherein the first fold line of said at least one first invertible flap is reinforced by being fused with the absorption body or by a strip of additional material attached over said first fold line on an outer surface of said cover.

13. The tampon according to claim 1, wherein the second inner surface of said at least one second invertible flap is at least partly provided with at least one lubricating agent.

14. The tampon according to claim 13, wherein said lubricating agent is selected from the group consisting of: pectin, hyaluronic acids, glycerides, waxes, and polyvinyl alcohol.

15. The tampon according to claim 1, wherein the second inner surface of said at least one second invertible flap is at least partly provided with at least one active agent selected from the group consisting of: odour controlling agents, perfumes, lactic acid producing organisms, pain control agents, and sedatives and mixtures thereof.

16. The tampon according to claim 1, wherein the second slit system of said at least one second invertible flap is constituted by one slit extending from said second start point to said second end point along said second curve.

17. The tampon according to claim 1, wherein the second slit system of said at least one second invertible flap is constituted by at least two second slits and a second interruption between each pair of consecutive second slits, wherein each second slit and each second interruption extends along a respective part of the respective second curve, wherein each second interruption is constituted by a non-slitted portion of said cover, and wherein each second interruption is arranged to be broken during insertion of said tampon into the vagina of a user so as to enable folding of said second invertible flap around said second fold line.

18. The tampon according to claim 1, wherein the second curve of said at least one second invertible flap has another shape than a second curve of one or more other second invertible flaps of said plurality of second invertible flaps.

19. The tampon according to claim 1, wherein the second curve of said at least one second invertible flap is V-shaped.

20. The tampon according to claim 1, wherein the second curve of said at least one second invertible flap is U-shaped.

21. The tampon according to claim 1, wherein the second fold line of said at least one second invertible flap has at least a different length or a different orientation than a second fold line of one or more other second invertible flaps of said plurality of second invertible flaps.

22. The tampon according to claim 1, wherein the second fold line of said at least one second invertible flap extends in a direction at least essentially orthogonal to the longitudinal direction of said tampon.

23. The tampon according to claim 1, wherein the second fold line of said at least one second invertible flap is reinforced by being fused with the absorption body or by a strip of additional material attached over the second fold line on an outer surface of said cover.

* * * * *